United States Patent
Congdon et al.

(10) Patent No.: US 11,931,003 B2
(45) Date of Patent: Mar. 19, 2024

(54) MEDICAL DEVICES FOR AGENT DELIVERY AND RELATED METHODS OF USE

(71) Applicant: Boston Scientific Scimed, Inc., Maple Grove, MN (US)

(72) Inventors: Daniel Congdon, Hudson, MA (US); Amanda Lynn Smith, Boston, MA (US); Laurie A. Lehtinen, Boylston, MA (US); Andrew Pic, Northboro, MA (US); Jason Weiner, Grafton, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 177 days.

(21) Appl. No.: 17/109,510

(22) Filed: Dec. 2, 2020

(65) Prior Publication Data
US 2021/0161370 A1    Jun. 3, 2021

Related U.S. Application Data

(60) Provisional application No. 62/943,065, filed on Dec. 3, 2019.

(51) Int. Cl.
*A61B 1/00* (2006.01)
*A61B 1/005* (2006.01)
*A61B 1/015* (2006.01)

(52) U.S. Cl.
CPC ........ *A61B 1/0014* (2013.01); *A61B 1/00073* (2013.01); *A61B 1/00119* (2013.01);
(Continued)

(58) Field of Classification Search
CPC ............ A61B 1/00128; A61B 1/00119; A61B 1/00137; A61B 1/015; A61B 1/00068
See application file for complete search history.

(56) References Cited

U.S. PATENT DOCUMENTS

| 471,854 A | 3/1892 | Howard |
| 881,238 A | 3/1908 | Hasbrouck |

(Continued)

FOREIGN PATENT DOCUMENTS

| CN | 101401956 B | 11/2012 |
| DE | 60215438 T2 | 8/2007 |

(Continued)

OTHER PUBLICATIONS

Bridevaux, Pierre-Olivier, et al. "Short-term safety of thoracoscopic talc pleurodesis for recurrent primary spontaneous pneumothorax: a prospective European multicentre study." European Respiratory Journal 38.4 (2011): 770-773.

(Continued)

*Primary Examiner* — Matthew J Kasztejna
(74) *Attorney, Agent, or Firm* — Bookoff McAndrews, PLLC

(57) ABSTRACT

A delivery device may be configured to deliver an agent to a target tissue through a channel of a medical device, the delivery device may include a body including (a) a coupling region configured to removably attach to a handle of the medical device, and (b) a coupler including an exit port for aligning with a port of the channel, wherein the coupler is configured to mate with the port of the channel; a source of an agent; and a source of pressurized fluid. The body, the source of agent, and the source of pressurized fluid may be arranged to deliver agent and pressurized fluid to the exit port for delivery through the channel.

20 Claims, 2 Drawing Sheets

(52) U.S. Cl.
CPC ...... *A61B 1/00128* (2013.01); *A61B 1/00137* (2013.01); *A61B 1/0052* (2013.01); *A61B 1/015* (2013.01)

(56) References Cited

U.S. PATENT DOCUMENTS

| | | | |
|---|---|---|---|
| 1,145,520 A | 7/1915 | Smith | |
| 1,599,959 A | 9/1926 | Buheiji | |
| 1,732,566 A | 10/1929 | McKendrick | |
| 2,151,418 A | 3/1939 | Bolté | |
| 2,185,927 A | 6/1940 | Shelanski | |
| 2,478,715 A | 8/1949 | Schmitt | |
| 2,623,519 A | 12/1952 | Cohen | |
| 3,669,113 A | 6/1972 | Altounyan et al. | |
| 3,940,061 A | 2/1976 | Gimple et al. | |
| 4,184,258 A | 6/1980 | Barrington et al. | |
| 4,427,450 A | 1/1984 | Kostansek | |
| 4,457,329 A | 7/1984 | Werley et al. | |
| 4,806,167 A | 2/1989 | Raythatha | |
| 5,215,221 A | 6/1993 | Dirksing | |
| 5,231,983 A | 8/1993 | Matson et al. | |
| 5,273,531 A | 12/1993 | Knoepfler | |
| 5,312,331 A | 5/1994 | Knoepfler | |
| 5,312,333 A | 5/1994 | Churinetz et al. | |
| 5,366,122 A | 11/1994 | Guentert et al. | |
| 5,445,612 A | 8/1995 | Terakura et al. | |
| 5,470,311 A | 11/1995 | Setterstrom et al. | |
| 5,884,621 A | 3/1999 | Matsugi et al. | |
| 5,951,531 A | 9/1999 | Ferdman et al. | |
| 6,003,512 A | 12/1999 | Gerde | |
| 6,484,750 B1 | 11/2002 | Foos et al. | |
| 6,554,022 B2 | 4/2003 | Wakeman | |
| 6,589,087 B2 | 7/2003 | Mackal et al. | |
| 6,684,917 B2 | 2/2004 | Zhu et al. | |
| 6,708,712 B2 | 3/2004 | Wakeman | |
| 6,716,190 B1 | 4/2004 | Glines et al. | |
| 6,799,571 B1 | 10/2004 | Hughes et al. | |
| 7,178,547 B2 | 2/2007 | Mackal | |
| 7,198,599 B2 * | 4/2007 | Goto | A61B 18/1492 600/154 |
| 7,311,270 B2 | 12/2007 | Kapila | |
| 7,334,598 B1 | 2/2008 | Hollars | |
| 7,361,300 B2 | 4/2008 | Kelly et al. | |
| 7,427,607 B2 | 9/2008 | Suzuki | |
| 7,455,248 B2 | 11/2008 | Kablik et al. | |
| 7,461,649 B2 | 12/2008 | Gamard et al. | |
| 7,544,177 B2 | 6/2009 | Gertner | |
| 7,563,299 B2 | 7/2009 | Baptista da Costa et al. | |
| 7,673,647 B2 | 3/2010 | Mackal | |
| 7,841,338 B2 | 11/2010 | Dunne et al. | |
| 7,892,205 B2 | 2/2011 | Palasis et al. | |
| 7,921,874 B2 | 4/2011 | Tekulve et al. | |
| 8,037,880 B2 | 10/2011 | Zhu et al. | |
| 8,097,071 B2 | 1/2012 | Burgess et al. | |
| 8,118,777 B2 | 2/2012 | Ducharme et al. | |
| 8,269,058 B2 | 9/2012 | McCarthy et al. | |
| 8,313,474 B2 | 11/2012 | Campbell et al. | |
| 8,360,276 B2 | 1/2013 | Rogier et al. | |
| 8,361,054 B2 | 1/2013 | Ducharme et al. | |
| 8,496,189 B2 | 7/2013 | Lomond et al. | |
| 8,673,065 B2 | 3/2014 | Burgess et al. | |
| 8,721,582 B2 | 5/2014 | Ji | |
| 8,728,032 B2 | 5/2014 | Ducharme et al. | |
| 8,741,335 B2 | 6/2014 | McCarthy | |
| 8,827,980 B2 | 9/2014 | Ji | |
| 8,910,627 B2 | 12/2014 | Iwatschenko et al. | |
| 8,951,565 B2 | 2/2015 | McCarthy | |
| 9,028,437 B2 | 5/2015 | Ott et al. | |
| 9,050,036 B2 * | 6/2015 | Poll | A61B 1/313 |
| 9,089,658 B2 | 7/2015 | Dunne et al. | |
| 9,101,744 B2 | 8/2015 | Ducharme | |
| 9,107,668 B2 | 8/2015 | Melsheimer et al. | |
| 9,132,206 B2 | 9/2015 | McCarthy | |
| 9,204,957 B2 | 12/2015 | Gregory et al. | |
| 9,205,170 B2 | 12/2015 | Lucchesi et al. | |
| 9,205,207 B2 | 12/2015 | Ji | |
| 9,205,240 B2 | 12/2015 | Greenhalgh et al. | |
| 9,308,584 B2 | 4/2016 | Burgess et al. | |
| 9,310,812 B2 | 4/2016 | Costle et al. | |
| 9,375,533 B2 | 6/2016 | Ducharme et al. | |
| 9,492,646 B2 | 11/2016 | Hoogenakker et al. | |
| 9,517,976 B2 | 12/2016 | Mackal | |
| 9,545,490 B2 | 1/2017 | Iwatschenko et al. | |
| 9,555,185 B2 | 1/2017 | Foster et al. | |
| 9,629,966 B2 | 4/2017 | Ji | |
| 9,636,470 B2 | 5/2017 | Pohlmann et al. | |
| 9,707,359 B2 | 7/2017 | Kubo | |
| 9,713,682 B2 | 7/2017 | Eistetter et al. | |
| 9,717,897 B2 | 8/2017 | Rogier | |
| 9,821,084 B2 | 11/2017 | Diegelmann et al. | |
| 9,839,772 B2 | 12/2017 | Ducharme | |
| 9,839,774 B2 | 12/2017 | Bonaldo | |
| 9,846,439 B2 | 12/2017 | Carman et al. | |
| 9,867,931 B2 | 1/2018 | Gittard | |
| 9,976,660 B2 | 5/2018 | Stanton et al. | |
| 10,004,690 B2 | 6/2018 | Lee et al. | |
| 10,010,705 B2 | 7/2018 | Greenhalgh et al. | |
| 10,017,231 B2 | 7/2018 | Fawcett, Jr. | |
| 10,036,617 B2 | 7/2018 | Mackal | |
| 10,065,004 B2 | 9/2018 | Eder et al. | |
| 10,173,019 B2 * | 1/2019 | Kaufmann | A61M 16/202 |
| 10,384,049 B2 | 8/2019 | Stanton et al. | |
| 10,441,761 B2 * | 10/2019 | Christakis | A61M 1/304 |
| 10,463,811 B2 | 11/2019 | Lee et al. | |
| 10,507,293 B2 | 12/2019 | Goodman et al. | |
| 10,646,706 B2 | 5/2020 | Rogier | |
| 10,730,595 B2 | 8/2020 | Fawcett | |
| 10,751,523 B2 | 8/2020 | Rogier | |
| 10,806,853 B2 | 10/2020 | Gittard | |
| 10,850,814 B2 | 12/2020 | Fawcett | |
| 10,994,818 B2 | 5/2021 | Hernandez | |
| 2003/0018238 A1 * | 1/2003 | Obata | A61B 1/12 600/179 |
| 2003/0032862 A1 * | 2/2003 | Ota | A61B 1/015 600/158 |
| 2003/0040658 A1 * | 2/2003 | Sano | A61B 1/127 600/156 |
| 2003/0045779 A1 * | 3/2003 | Ito | A61B 1/127 600/156 |
| 2004/0107963 A1 | 6/2004 | Finlay et al. | |
| 2004/0249359 A1 | 12/2004 | Palasis et al. | |
| 2005/0121025 A1 | 6/2005 | Gamard et al. | |
| 2005/0147656 A1 | 7/2005 | McCarthy et al. | |
| 2005/0220721 A1 | 10/2005 | Kablik et al. | |
| 2006/0004314 A1 | 1/2006 | McCarthy et al. | |
| 2006/0213514 A1 | 9/2006 | Price et al. | |
| 2006/0229498 A1 * | 10/2006 | Kohno | A61B 1/00068 600/158 |
| 2007/0056586 A1 | 3/2007 | Price et al. | |
| 2007/0066920 A1 | 3/2007 | Hopman et al. | |
| 2007/0066924 A1 | 3/2007 | Hopman et al. | |
| 2007/0082023 A1 | 4/2007 | Hopman et al. | |
| 2007/0125375 A1 | 6/2007 | Finlay et al. | |
| 2007/0151560 A1 | 7/2007 | Price et al. | |
| 2007/0083137 A1 | 8/2007 | Hopman et al. | |
| 2007/0199824 A1 | 8/2007 | Hoerr et al. | |
| 2008/0021374 A1 | 1/2008 | Kawata | |
| 2008/0287907 A1 | 11/2008 | Gregory et al. | |
| 2009/0101144 A1 | 4/2009 | Gamard et al. | |
| 2009/0155342 A1 | 6/2009 | Diegemann et al. | |
| 2009/0281486 A1 * | 11/2009 | Ducharme | A61M 5/1409 604/147 |
| 2010/0121261 A1 | 5/2010 | Kablik et al. | |
| 2010/0305505 A1 | 12/2010 | Ducharme et al. | |
| 2011/0073200 A1 | 3/2011 | Overvaag et al. | |
| 2011/0178495 A1 * | 7/2011 | Ji | A61M 15/0016 606/213 |
| 2011/0274726 A1 | 11/2011 | Guo et al. | |
| 2011/0282381 A1 | 11/2011 | Cronin et al. | |
| 2011/0308516 A1 | 12/2011 | Price et al. | |
| 2014/0271491 A1 | 9/2014 | Gittard et al. | |
| 2015/0094649 A1 * | 4/2015 | Gittard | A61M 11/02 428/402 |

(56) References Cited

U.S. PATENT DOCUMENTS

| | | | |
|---|---|---|---|
| 2015/0125513 A1 | 5/2015 | McCarthy | |
| 2016/0375202 A1 | 12/2016 | Goodman et al. | |
| 2017/0106181 A1 | 4/2017 | Bonaldo et al. | |
| 2017/0232141 A1 | 8/2017 | Surti et al. | |
| 2017/0252479 A1 | 9/2017 | Ji et al. | |
| 2017/0296760 A1 | 10/2017 | Lee et al. | |
| 2018/0099088 A1 | 4/2018 | Gittard | |
| 2018/0193574 A1 | 7/2018 | Smith et al. | |
| 2018/0214160 A1 | 8/2018 | Hoskins et al. | |
| 2018/0339144 A1 | 11/2018 | Greenhalgh et al. | |
| 2019/0134366 A1 | 5/2019 | Erez et al. | |
| 2019/0217315 A1 | 7/2019 | Maguire et al. | |
| 2019/0232030 A1 | 8/2019 | Pic et al. | |
| 2020/0100986 A1* | 4/2020 | Pic | G05D 16/107 |
| 2021/0024187 A1 | 1/2021 | Fawcett et al. | |
| 2021/0069485 A1 | 3/2021 | Rogier | |
| 2021/0162122 A1* | 6/2021 | Pic | A61B 17/00491 |
| 2021/0379302 A1* | 12/2021 | Sigmon, Jr. | A61J 1/2058 |

FOREIGN PATENT DOCUMENTS

| | | |
|---|---|---|
| EP | 3052168 B1 | 11/2019 |
| JP | H07118305 A | 5/1995 |
| WO | 03013552 A1 | 2/2003 |
| WO | 2004066806 A2 | 8/2004 |
| WO | 2005062896 A2 | 7/2005 |
| WO | 2006071649 A2 | 7/2006 |
| WO | 2006088912 A2 | 8/2006 |
| WO | 2007020624 A1 | 2/2007 |
| WO | 2008033462 A2 | 3/2008 |
| WO | 2009061409 A1 | 5/2009 |
| WO | 2015050814 A1 | 4/2015 |
| WO | 2018157772 A1 | 9/2018 |

OTHER PUBLICATIONS

Giday, Samuel, et al. "Safety analysis of a hemostatic powder in a porcine model of acute severe gastric bleeding." Digestive diseases and sciences 58.12 (2013): 3422-3428.
Giday, Samuel A., et al. "A long-term randomized controlled trial of a novel nanopowder hemostatic agent for control of severe upper gastrointestinal bleeding in a porcine model." Gastrointestinal Endoscopy 69.5 (2009): AB133.
Giday, S. A., et al. "Long-term randomized controlled trial of a novel nanopowder hemostatic agent (TC-325) for control of severe arterial upper gastrointestinal bleeding in a porcine model." Endoscopy 43.04 (2011): 296-299.
Regalia, Kristen, et al. "Hemospray in Gastrointestinal Bleeding." Practical Gastroenterology. Endoscopy: Opening New Eyes, ser. 8, May 2014, pp. 13-24. 8.
Cook Medical. Hemospray Endoscopic Hemostat, Cook, 2014. (7 pages, in English).
"Hemospray Clinical Experience Shows Efficacy of a New Hemostasis Modality—v1", Cook Medical, 2012.
"Hemospray Clinical Experience Shows Efficacy of a New Hemostasis Modality—v2", Cook Medical, 2013.
"Hemospray Clinical Experience Shows Efficacy of a New Hemostasis Modality—v3", Cook Medical, 2014.
Aslanian, Harry R., and Loren Laine. "Hemostatic powder spray for GI bleeding." Gastrointestinal endoscopy 77.3 (2013): 508-510.
Giday, S. A., et al. "Long-term randomized controlled trial of a novel nanopowder hemostatic agent (TC-325) for control of severe arterial upper gastrointestinal bleeding in a porcine model." Endoscopy 43.04 (2011): 296-299. via ResearchGate.
RETSCH GmbH Haan. Sieve Analysis: Taking a Close Look at Quality, An Expert Guide to Particle Size Analysis. 2015. (56 pages, in English).
Micromeritics. Density Analysis, 2001. (6 pages, in English).
Micromeritics. "Application Note: Bulk and Skeletal Density Computations for the AutoPore." May 2012. (3 pages, in English).
Arefnia, Ali, et al. "Comparative Study on the Effect of Tire-Derived Aggregate on Specific Gravity of Kaolin." Electronic Journal of Geotechnical Engineering 18 (2013): 335-44.
Kesavan, Jana, et al. "Density Measurements of Materials Used in Aerosol Studies". Edgewood Chemical Biological Center Aberdeen Proving Ground MD, 2000.
International Search Report and Written Opinion dated Mar. 19, 2021 in counterpart International Patent Application No. PCT/US2020/062861 (11 pages, in English).

* cited by examiner

MEDICAL DEVICES FOR AGENT DELIVERY AND RELATED METHODS OF USE

CROSS-REFERENCE TO RELATED APPLICATIONS

This application claims the benefit of priority from U.S. Provisional Application No. 62/943,065, filed Dec. 3, 2019, which is incorporated by reference herein in its entirety.

TECHNICAL FIELD

The present disclosure relates generally to medical systems and devices for delivering pressurized fluids/agents, and more particularly, to devices, methods and tools for delivering the fluid/agent through a channel of a medical device.

BACKGROUND

In certain medical procedures, it may be necessary to stop or minimize bleeding internal to the body. For example, an endoscopic medical procedure may require hemostasis of bleeding tissue within the gastrointestinal tract, for example in the esophagus, stomach, or intestines.

During an endoscopic procedure, a user inserts a sheath of an endoscope into a body lumen of a patient. The user utilizes a handle of the endoscope to control the endoscope during the procedure. Tools are passed through a working channel of the endoscope via, for example, a port in the handle, to deliver treatment at the procedure site near a distal end of the endoscope. The procedure site is remote from the operator.

To achieve hemostasis at the remote site, a hemostatic agent may be delivered by a device inserted into the working channel of the endoscope. Agent delivery may be achieved through mechanical systems, for example. Such systems, however, may require numerous steps or actuations to achieve delivery, may increase procedure time, may not achieve a desired rate of agent delivery or a desired dosage of agent, may require the user to readjust positioning of the endoscope to allow passage of the device through the working channel, may result in the agent clogging portions of the delivery device, may result in inconsistent dosing of agent, or may not result in the agent reaching the treatment site deep within the GI tract. The current disclosure may solve one or more of these issues or other issues in the art.

SUMMARY OF THE DISCLOSURE

Examples of the present disclosure relate to, among other things, agent delivery devices. Each of the examples disclosed herein may include one or more of the features described in connection with the disclosed examples.

A delivery device may be configured to deliver an agent to a target tissue through a channel of a medical device, the delivery device may include a body including (a) a coupling region configured to removably attach to a handle of the medical device, and (b) a coupler including an exit port for aligning with a port of the channel, wherein the coupler is configured to mate with the port of the channel; a source of an agent; and a source of pressurized fluid. The body, the source of agent, and the source of pressurized fluid may be arranged to deliver agent and pressurized fluid to the exit port for delivery through the channel.

Any of the systems and devices disclosed herein may have any of the following features. The coupling region may include a U-shaped surface configured to mate with a handle of the medical device. The U-shaped surface may include features to inhibit movement between the U-shaped surface and the handle of the medical device. The coupling region may be configured to snap-fit onto the handle of the medical device. The coupling region may include a strap configured to wrap around the handle of the medical device. The handle of the medical device may be a first handle, and the body may include a second handle. The second handle may include an interior portion configured to receive a pressurized fluid container. A longitudinal axis of the second handle may extend substantially parallel to a longitudinal axis of the first handle when the delivery device is coupled to the first handle. The second handle may be spaced from the first handle when the delivery device is coupled to the first handle. The second handle may include grooves configured to accommodate fingers of a user's hand, and an axis extending through the grooves may be substantially parallel to an axis of the first handle. The coupler may be configured to form a fluid tight seal with the port of the channel such that the exit port is fluidically connected to the channel. The coupler may be a press-fit coupler configured to press fit onto the port to form a fluid tight seal with the port. The coupler may be a first coupler and the exit port may be a first exit port, and the device may further include a first catheter fluidically coupled to the first coupler at a first end; a y-connector fluidically coupled to a second end of the first catheter; a syringe fluidically coupled to the y-connector; and a second coupler including a second exit port for aligning with a port of the channel. The second exit port may be fluidically connected to the first catheter, the y-connector, and the syringe; and the second coupler may be configured to mate with the port of the channel. The device may further include a second catheter including a third coupler, wherein the second catheter is fluidically connected to the y-connector, coupled to the second coupler, and the third coupler is configured to mate with the port of the channel. The handle of the medical device may be a first handle, and the body may include a first proximal portion including a second handle, a first distal portion, and a second proximal portion including the coupling region; and the first proximal portion, the second proximal portion, and the first distal portion may form a U-shape.

A delivery device may be configured to deliver an agent to a target tissue through a channel of a medical device, the delivery device may include: 1) a body including (a) a coupling region configured to removably attach to a handle of the medical device, and (b) a coupler including an exit port for aligning with a port of the channel, the coupler may be configured to mate with the port of the channel; 2) an enclosure within the body and configured to store an agent, receive a pressurized fluid, and release a combination of the pressurized fluid and the agent through the exit port; and 3) a regulator within the body and configured to control delivery of pressurized fluid to the enclosure, the regulator including a fluid input port, wherein pressurized fluid and agent flows from the enclosure to the exit port upon coupling a pressurized fluid container to the fluid input port.

Any of the systems and devices disclosed herein may have a total volume of pressurized fluid within the pressurized fluid container is configured to deploy a preset amount of the agent through the channel.

In other examples, a system configured to deliver an agent to a target tissue through a channel of a medical device, the system may include the medical device comprising a handle, the channel, and a port at an end of the channel; and a delivery device. The delivery device may include a body including (a) a coupling region configured to removably attach to the handle; and (b) a coupler including an exit port for aligning with the port, wherein the coupler is configured to mate with the port; a source of an agent; and a source of pressurized fluid, wherein the body, the source of agent, and the source of pressurized fluid may be arranged to deliver agent and pressurized fluid to the exit port and the channel for delivery to target tissue.

Any of the systems and devices disclosed herein may have any of the following features. The delivery device may be configured to deliver agent and pressurized fluid through the channel such that the agent contacts an interior surface of the channel. The system or device may include a liner covering an exterior surface of the medical device and an interior surface of the channel.

It may be understood that both the foregoing general description and the following detailed description are exemplary and explanatory only and are not restrictive of the invention, as claimed. As used herein, the terms "comprises," "comprising," or any other variation thereof, are intended to cover a non-exclusive inclusion, such that a process, method, article, or apparatus that comprises a list of elements does not include only those elements, but may include other elements not expressly listed or inherent to such process, method, article, or apparatus. The term "exemplary" is used in the sense of "example," rather than "ideal." The term "approximately," or like terms (e.g., "substantially"), includes values +/−10% of a stated value. The term "distal" refers to a portion farthest away from a user when introducing a device into a patient. By contrast, the term "proximal" refers to a portion closest to the user when placing the device into the patient. Proximal and distal directions are labeled with arrows marked "P" and "D", respectively, throughout the figures.

BRIEF DESCRIPTION OF THE DRAWINGS

The accompanying drawings, which are incorporated in and constitute a part of this specification, illustrate various exemplary embodiments and together with the description, serve to explain the principles of the disclosed embodiments.

DETAILED DESCRIPTION

An agent delivery device used in exemplary embodiments may be configured to house an agent within a housing of the delivery device and may be configured to control a rate at which an agent and a fluid leave the delivery device. The delivery device may be configured to house single component agents or multi-component agents. In the case of multi-component agents, the delivery device may be configured to allow for mixing of the components, prior to delivery from the device. Various mechanisms may be utilized in order to pre-pressurize a chamber of the agent and actuate the delivery device to deliver the agent. These mechanisms may include pneumatics, wires, tubes, valves, or any suitable combination thereof. Such agent delivery devices may be configured to couple to primary medical devices and may work cooperatively with primary medical devices to deliver an agent to a target tissue. For example, some embodiments of delivery devices combined with a primary medical device, such as one already positioned within a body lumen and at a target site, may facilitate delivering a hemostatic agent through a channel of the medical device to target tissue within a body of a patient.

Figure 1:
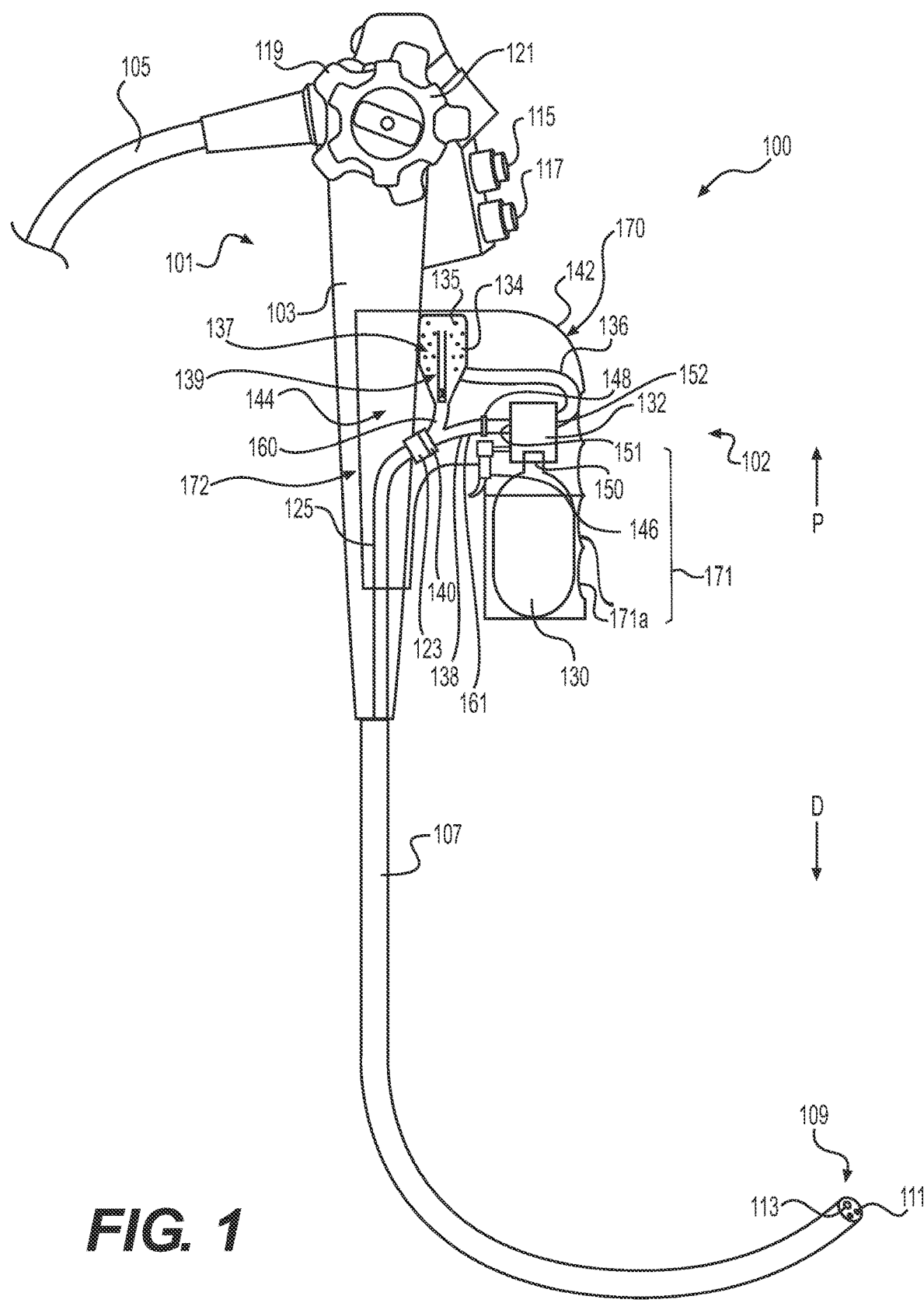
FIG. 1 is a side view of a delivery system according to an exemplary embodiment.

Referring to FIG. 1, a delivery system 100 according to an embodiment is shown. Delivery system 100 may include a medical device 101 and a delivery device 102. Medical device 101 may be considered a primary medical device, and delivery device 102 may be configured to couple to and operate with medical device 101. Medical device 101 may be an endoscope, a ureteroscope, a hysteroscope, a uteroscope, a bronchoscope, a colonoscope, a cystoscope, and any other medical device known in the art having a channel therethrough. Medical device 101 may include a handle 103, a catheter 107, one or more operating knobs 119, 121, one or more valves/actuators 115, 117, and an umbilicus 105. A channel 125 may be a working channel, may extend distally from a proximal port 123 through a portion of handle 103, and may extend through catheter 107 to a distal opening 111 at distal end 109. Channel 125 may be configured to receive one or more tools, fluids, and/or suction applied at proximal port 123 or through umbilicus 105. In some examples, medical device 101 may include an imaging unit 113 positioned at a distal end 109 of catheter 107. In some examples, umbilicus 105 may be electronically coupled to a control unit (not shown) and one or more actuators 115, 117 may actuate a command executed by the control unit, such as activating a fluid jet, suction, or activating an image capture mechanism using imaging unit 113. In some examples, umbilicus 105 may couple one or more fluid sources to medical device 101 and/or may couple one or more vacuum sources to medical device 101. In some examples, one or more knobs 119, 121 may be configured to control movement of distal end 109 of catheter 107.

Delivery device 102 may be configured to removably couple to medical device 101. Delivery device 102 may include a housing 142, an enclosure 134 containing an agent 135, a fluid container 130, a regulator 132 including a fluid source input port 150, an actuator 146, a filter 148, a coupler 140, and a plurality of tubes 136, 138. In some examples, fluid container 130 may release pressurized fluid into regulator 132 when coupled to regulator 132. For example, input port 150 may be configured to pierce fluid container 130 when fluid container 130 is coupled to regulator 132, releasing pressurized fluid from fluid container 130 into regulator 132. These components and their functions will be discussed below. These components, however, are exemplary. For example, any of the devices and/or their components that are described in U.S. patent application Ser. No. 16/589,633, filed Oct. 1, 2019, may be used in embodiments. The entire contents of that application are incorporated herein.

With reference to FIG. 1, fluid container 130 is configured to contain a fluid, such as a gas, e.g., carbon dioxide or any other gas or other fluid known in the art. While shown as a cylindrical enclosure, fluid container 130 may be any shape, such as a torpedo-shape, a sphere, or any other shape known in the art and used for storing fluid. In some examples, fluid container 130 could be a carbon dioxide tank or cylinder typically found in medical settings, such as a hospital. Fluid container 130 may include one or more outer walls defining one or more inner chambers (not shown), the inner chamber(s) configured to contain the fluid. The walls of fluid container 130 may be formed of any material suitable for containing the fluid, such as but not limited to a metal alloy, a ceramic, or other material known in the art. The fluid contained in the inner chamber of fluid container 130 may be under pressure. Accordingly, the walls are formed of a material and/or a thickness suitable to contain the fluid at a pressure of, for example, at least approximately 1000 pounds per square inch (PSI), or approximately 850 PSI. For example, gases which may be contained in fluid container 130 may include carbon dioxide (CO2) having a vapor pressure of approximately 2,000-8,000 kPa at typical device temperatures, or nitrogen (N2) having a vapor pressure less than 40 MPa at typical device temperatures. It will be understood that these gases are examples and are not limiting to the types of gases contained in fluid container 106.

With continued reference to FIG. 1, fluid container 130 is attached to regulator 132 at regulator input port 150. Regulator 132 includes input port 150 and one or more output ports 151, 152. Input port 150 of regulator 132 may be configured to pierce fluid container 130. One or more tubes 136, 138 may fluidically couple one or more output ports 151, 152 to enclosure 134 and/or coupler 140. Regulator 132 may be configured to change the flow rate of fluid exiting fluid container 130 such that fluid flows through tubes 136, 138 into enclosure 134 and/or coupler 140 at a selected flow rate. In some examples, fluid may enter enclosure 134 and/or coupler 140 at a flow rate in the inclusive range of four standard liters per minute to twelve standard liters per minute of fluid flow. In some examples, delivery device 102 may be configured to operate with fluid flowing through enclosure 134 and/or coupler 140 at a flow rate in the inclusive range of between five standard liters per minute to ten standard liters per minute.

Fluid container 130 may be coupled to regulator 132 via a pull-cord coupling mechanism or a pump mechanism. In some examples, a pull-cord coupling mechanism may be included in delivery device 102 and may include an actuator including a cord and pin, and the pin may engage a fluid cartridge (such as fluid container 130) to release fluid from the cartridge when a user pulls the cord. For example, the pin may puncture the cartridge and result in pressurized fluid flowing in device 102. In other examples, a pump mechanism may be included in device 102 and may be configured to supply pressurized fluid to device 102, for example by supplying pressurized gas in device 102. In some examples, device 102 may not include regulator 132 and container 130 may be coupled directed to one or more tubes 136, 138 via an input opening similar to input opening 150.

Tube 136 may supply fluid under pressure from fluid container 130 and regulator 132 to enclosure 134. Enclosure 134 may be cylindrical and may include an interior cavity 137 and a funnel portion 139 at an end of enclosure 134. Enclosure 134 may be configured to store an agent 135, such as a powder or liquid medicament, within interior cavity 137, and interior cavity 137 may be fluidically connected to tube 136. Funnel portion 139 may include tapered surfaces forming a portion of interior cavity 137 that lead to an opening at an end of enclosure 134. Funnel portion 139 may be configured to direct agent 135 through the opening into tube 138 (branch 160 of tube 138) and coupler 140. In some examples, enclosure 134 may be configured to gravity feed agent 135 into tube 138 and coupler 140. Enclosure 134 may be any suitable material known in the art. In some examples, enclosure 134 may be made of a transparent material.

Tube 138 may include two branches 160, 161. Branch 160 may extend between and fluidically couple enclosure 134 and coupler 140. Branch 161 may extend between and fluidically couple regulator 132 and coupler 140. Branch 160 and branch 161 may merge at, or just prior to, coupler 140. In some examples, tube 138 may include a filter 148 positioned within a lumen of tube 138. Filter 148 may be configured to allow fluid flow from the regulator 132 distally through the lumen of tube 138, and may also be configured to prevent movement of agent 135 proximally through tube 138, towards regulator 132. Filter 148 may be configured to prevent movement of agent 135 through tube 138 into regulator 132. In some examples, filter 148 may be configured to restrict fluid flow through tube 138 by narrowing the diameter of the interior lumen of tube 138. Delivery device 102 may provide a means to deliver agent 135 to a target tissue by using an existing channel on a medical device, such as channel 125 of medical device 101, which may reduce procedure time and may simplify a procedure requiring delivery of an agent 135 to tissue.

Actuator 146 may be operatively coupled to regulator 132 and may be configured to control the release of pressurized fluid from regulator 132 into tube 136 and/or tube 138. Actuator 146 may include a trigger, a button, a pressure sensor, a lever, and/or any other actuation mechanism known in the art. In some examples, actuator 146 may be configured to control the release of agent 135 into coupler 140 and into channel 125 of medical device 101 via regulation of pressurized fluid applied to tube 136 and enclosure 134. Actuator 146 may extend outward from housing 142 to allow a user to actuate actuator 146.

Coupler 140 may be configured to releasably couple to port 123 of channel 125 and fluidically connect tube 138 with channel 125. In some examples, coupler 140 may form a fluid-tight seal between port 123 and coupler 140 such that fluid may pass through tube 138 into channel 125 without flowing to an area exterior to medical device 101 and delivery device 102. Coupler 140 may include one or more o-rings which may be polymer, rubber, metal, or any other material. In some examples, coupler 140 may be a press-fit coupler and may form a fluid tight seal with port 123, and fluidically couple tube 138 to channel 125. In some examples, coupler 140 may be a quick-release coupler. Coupler 140 may be a gasket seal such as a rubber gasket seal or a snap fitting. In some examples, coupler 140 may be a deformable plastic cap that may be pinched by the user to open, placed on port 123, and released by the user to close onto port 123. Coupler 140 may include a screw down component (e.g. may include threads that may couple to port 123 via the threads of the coupler 140 mating with threads of the port 123), and the geometry at the distal portion of handle 103 may facilitate coupler 140 coupling to port 123.

Each of enclosure 134, fluid container 130, regulator 132, actuator 146, filter 148, coupler 140, and tubes 136, 138 may be fully or partially contained within housing 142. Housing 142 may be U-shaped (an upside-down "U" as shown in the Figure) and may include a proximal portion 170, a first distal portion 171, and a second distal portion 172. First distal portion 171 (at the bottom right of housing 142) may be a handle and may be configured for a user to hold using a hand. In some examples, a central longitudinal axis of first distal portion 171 may be configured to extend parallel to a central longitudinal axis of handle 103. In some examples, proximal portion 170 may contact and extend radially-outward from handle 103 when delivery device 102 is coupled to handle 103, and first distal portion 171 may be spaced from handle 103. First distal portion 171 may include an outer surface ergonomically shaped to accommodate one or more fingers of a user's hand. For example, each of grooves 171a on a surface farthest from device 101 can accommodate four fingers of an operator's hand, while another hand of the operator holds handle 103 of device 101.

A portion of first distal portion 171 may be removable and may be configured to allow insertion of fluid container 130 into housing 142 for coupling to regulator 132. All or a portion of fluid container 130 may be positioned within first distal portion 171. In some examples, a removable cover (not shown) may be at a proximal end of housing 142 and may be configured to allow a user to access enclosure 134.

A coupling region 144 of housing 142 may be configured to removably couple to handle 103 of medical device 101. In some examples, coupling region 144 may be configured to snap-fit onto handle 103. Coupling region 144 may include coupler 140 and may be configured to couple to handle 103 such that coupler 140 aligns with proximal opening 123 of channel 125. That surface receives handle 103 of device 101. In some examples, coupling region 144 may include a U-shaped surface extending longitudinally in a proximal-distal direction. In some examples, coupling region 144 may include a strap (not shown) configured to wrap around handle 103 and couple delivery device 102 to handle 103. In some examples, coupling region 144 may be configured to generate an audible sound, such as a "click", when delivery device 102 has been fixedly coupled to handle 103. In other embodiments, the inner U-shaped surface of coupling region 144 may include friction enhancing features to inhibit movement between that surface and handle 103. Coupling region 144 may include a deformable plastic component that may deform and return to its original state, in order to facilitate coupling coupling region 144 to handle 103, and coupling region 144 may have an original state that matches the form factor of handle 103. In some examples, coupling region 144 may include a C-shaped surface that may be configured to snap onto handle 103 and extend circumferentially around handle 103. Coupling region 144 may include a hinged portion (not shown) configured to surround handle 103 and couple to a portion of coupling region 144 once positioned around handle 103. For example, coupling region 144 may include a hinged portion that has a first state in which the hinge is open and coupling region 144 may be positioned around handle, and a second state when the hinged portion extends around a portion of handle 103 and a portion of the coupling region 144 couples to another, different portion of coupling region 144 (which may form a portion extending circumferentially around handle 103). A hinged portion of coupling region 144 may fully encircle the radially-outer surface extending around the central longitudinal axis of handle 103. In some examples, a hinged portion of coupling region 144 may partially encircle the radially-outer surface of handle 103, extending around the central longitudinal axis of handle 103, when coupling region 144 is coupled to handle 103.

In operation, if delivery device is not already loaded with an enclosure 134 with agent 135, a user may first insert an agent 135 into enclosure 134 of delivery device 102. The user may then, in some examples, couple fluid container 130 to regulator 132. The user may then couple delivery device 102 to medical device 101 by, in some examples, pushing coupling region 144 towards handle 103, or in any other way described above. The user may then, in some examples, move delivery device 102 proximally and/or distally until coupler 140 fluidically couples to port 123 of channel 125, in any of the ways described above. If device 101 has not already been inserted into the patient with distal opening proximate target tissue, the user may then position distal opening 111 of channel 125 proximate to target tissue of a patient, for example target tissue within a body lumen of a patient. Once distal opening 111 is positioned proximate to or at the target tissue, the user may actuate actuator 146. By actuating actuator 146, regulator 132 may initiate fluid flow from fluid container 130 through regulator 132 and into tube 136. Fluid may then flow from tube 136 through enclosure 134. When fluid flows into enclosure 134, agent 135 may be moved in the direction of fluid flow and carried through tube 138 and coupler 140, and into port 123 and channel 125. Agent 135 may then be deployed through channel 125 and propelled out of distal opening 111 towards the target tissue via the fluid flow. In some examples, after delivering agent 135 to target tissue, a user may then disconnect delivery device 102 from handle 101 and clean channel 125 by extending a wire brush or other cleaning brush through channel 125, or supplying an irrigation fluid through channel 125. A user may then re-couple delivery device 102 to handle 103, and continue delivering agent 135 to target tissue through channel 125.

In some examples, medical device 101 may include a suction channel including a proximal port similar to proximal opening 123 or extending through umbilicus 105 to a suction enclosure, for example. To operate delivery device 102 with such a suction channel, the user may first press an actuator 115, 117 to prevent suction from flowing through the suction channel. The user may then couple delivery device 102 to the proximal port of the working channel for delivery of agent 135, as described above. By first turning off the application of suction to the suction channel, and thereby preventing suction through channel 125, the user may prevent agent 135 from coming into contact with bodily fluids and may avoid clogging of channel 125 while delivering agent 135 through channel 125.

In other examples, a user may initiate fluid flow through delivery device 102 when fluid container 130 is coupled to regulator 132, and a user does not need to actuate actuator 146 or otherwise adjust the deployment of agent 135 through channel 125 via fluid flow from fluid container 130. The actuation of delivery device 102 through coupling fluid container 130 to regulator 132 (for example, piercing a carbon dioxide container by coupling it to regulator 132) provides a means to deliver agent 135 to target tissue without the need for actuator 146 and may produce a single shot of agent 135 to target tissue. In some examples, delivery device 102 may not include regulator 107 and may not include actuator 146. In some examples, all of or the majority of agent 135 may be moved out of enclosure 134 when fluid container 130 is coupled to regulator 132. The volume of fluid container 130 may be configured to deploy a selected amount of agent 135 using delivery device 102.

Figure 2:
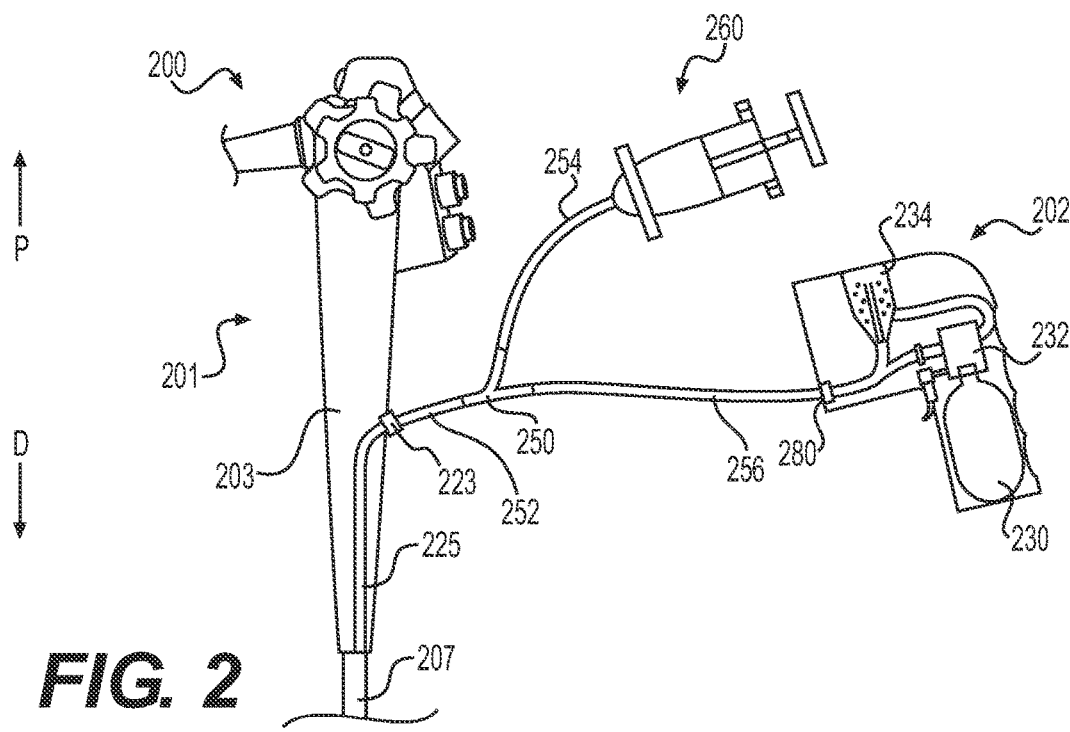
FIG. 2 is a side view of a delivery system according to an exemplary embodiment.

FIG. 2 shows an alternative embodiment of a delivery system 200 similar to delivery system 100. Delivery system 200 may include medical device 201 and delivery device 202. Medical device 201 may include handle 203, catheter 207, and channel 225 including proximal opening 223, like device 101. Delivery device 202 may include fluid container 230, regulator 232, and enclosure 234, like device 102. Any of the features described herein above regarding delivery system 100, medical device 101, and delivery device 102 may be included in delivery system 200, medical device 201, and delivery device 202.

Delivery system 200 may also include a catheter 256 (e.g. a tube) extending from an output port 280, which may or may not include a coupler similar to coupler 138. Catheter 256 may extend from output port 280 to a y-connector 250, and an end of catheter 256 may fluidically couple to y-connector 250. Y-connector 250 may also be fluidically coupled to a second catheter 254 (e.g. a tube) extending from y-connector 250 to a syringe 260. Y-connector 250 may also be fluidically coupled to a third catheter 252 (e.g. a tube)

extending from y-connector 250 to port 223 of channel 225. In some examples, an end of third catheter 252 may include a coupler similar to coupler 138 described herein above and may be configured to fluidically couple to port 223 of channel 225. In other examples of delivery system 200, y-connector 250 may be directly coupled to port 223 of channel 225 and may not include third catheter 252.

Syringe 260 may be configured to push fluid through second catheter 254, y-connector 250, third catheter 252, and into channel 225 through port 223. Syringe 260 may be configured to supply fluid to wash channel 225. In some examples, a user may deploy fluid into channel 225 via syringe 260 after delivering an agent from delivery device 202 through channel 225. Syringe 260 may provide a user a means to wash channel 225 immediately after delivery of an agent from delivery device 202 through channel 225 to target tissue of a patient. In some examples, syringe 260 may be configured to facilitate removal of a clog formed within channel 225, such as a build up of agent 135 within channel 225.

Figure 3:
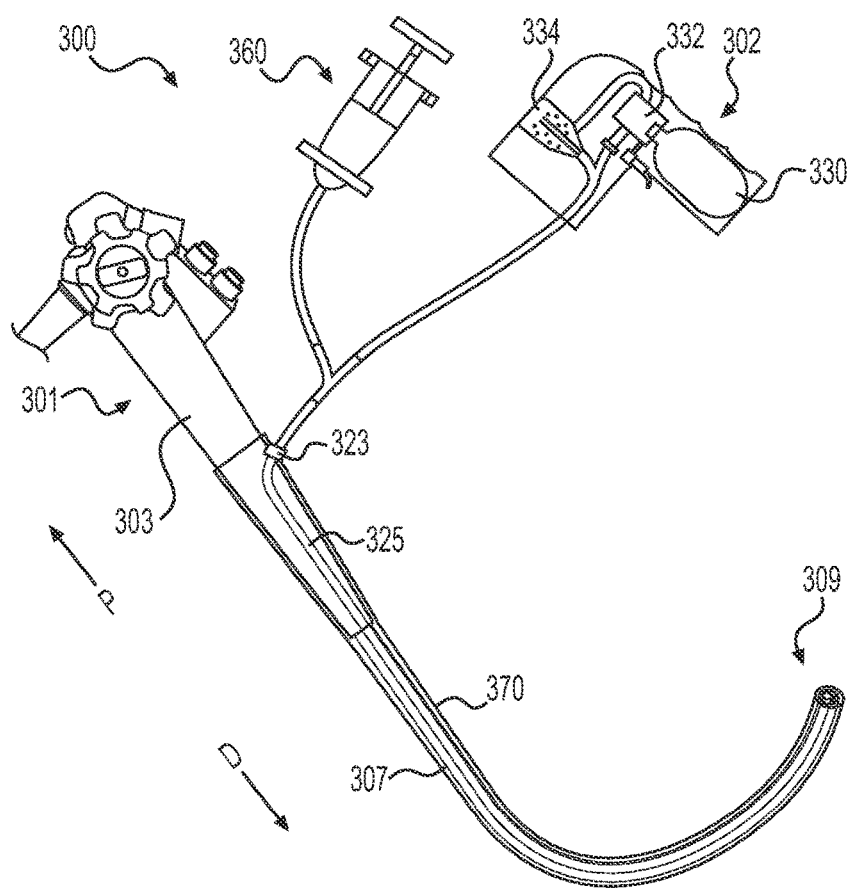
FIG. 3 is a side view of a delivery system according to an exemplary embodiment.

FIG. 3 shows an alternative embodiment of a delivery system 300. Delivery system 300 may include medical device 301, delivery device 302, and syringe 360. Medical device 301 may include handle 303, catheter 307, and channel 325 including proximal opening 323. Delivery device 302 may include fluid container 330, regulator 332, and enclosure 334. Any of the features described herein above regarding delivery systems 100, 200, medical devices 101, 201, and delivery devices 102, 202 may be included in delivery system 300, medical device 301, and delivery device 302.

Delivery system 300 also includes a medical device liner 370 extending longitudinally around catheter 307 and a distal portion of handle 303 including port 323. Medical device liner 370 may also extend through channel 325 such that portions of liner 370 are adjacent to the interior surface of channel 325. Medical device liner 370 may envelope a portion of medical device 301, including all of catheter 307, and may cover the exterior surface of that portion of medical device 301. In some examples, medical device liner 370 may include two cylindrical sleeve-like portions with a first portion configured to cover the exterior portion of catheter 307 and handle 303, and a second portion configured to cover, or otherwise line, the interior surface of channel 325. The first and second portions of device liner 370 may be connected at a distal end portion configured to cover distal tip 309. The second portion of device liner 370 (the portion within channel 325) may be configured to be back-fed through channel 325 from distal end 309. A portion of device liner 370 may be configured to removably couple to port 323. Medical device liner 370 may be configured to protect exterior portions of medical device 301 and also protect interior surfaces of channel 325 from abrasion that may be caused by moving agents through channel 325. Medical device liner 370 may be disposable and may be made of any suitable flexible material known in the art. In some examples, medical device liner 370 may be made of one or more of plastic, polymer, and pebax. Liner 370 may be fastened to proximal opening 323 via heat shrink, reflow of plastic components, or a barb fitting.

Unless described otherwise, the structural elements of medical devices 101, 201, 301 and delivery devices 102, 202, 302 may be any material known in the art, including but not limited to a metal alloy, a ceramic, and/or a resin.

It will be apparent to those skilled in the art that various modifications and variations can be made to the disclosed device without departing from the scope of the disclosure.

Other embodiments of the disclosure will be apparent to those skilled in the art from consideration of the specification and practice of the invention disclosed herein. It is intended that the specification and examples be considered as exemplary only, with a true scope and spirit of the invention being indicated by the following claims.

We claim:

1. A delivery device configured to deliver an agent to a target tissue through a channel of a medical device, the delivery device comprising:
    a body including (a) a coupling region configured to removably attach to a handle of the medical device, the medical device including an endoscope, and (b) a coupler including an exit port for aligning with a port of the channel, wherein the coupler is configured to mate with the port of the channel;
    a source of the agent defined by a cylindrical portion and a funnel portion positioned downstream from the cylindrical portion, the cylindrical portion is configured to store the agent and the funnel portion is configured to receive the agent from the cylindrical portion via gravity;
    a source of pressurized fluid disposed within the body, the cylindrical portion is in fluid communication with the source of pressurized fluid through the funnel portion; and
    an actuator including a trigger that is movably coupled to the body, wherein, in response to pulling the actuator, the body, the source of the agent, and the source of pressurized fluid are arranged to deliver the pressurized fluid through the funnel portion upstream into the cylindrical portion of the source of agent to move the agent therein, and to move a mixture of the agent and the pressurized fluid out of the source of the agent and to the exit port for delivery through the channel;
    wherein the actuator is configured to move a pin relative to the body and into engagement with the source of pressurized fluid, in response to selectively pulling the actuator, thereby piercing the source of pressurized fluid and releasing the pressurized fluid into the source of the agent.

2. The device according to claim 1, wherein the coupling region is configured to mate with the handle of the medical device.

3. The device according to claim 1, wherein the coupling region includes features configured to inhibit movement between the coupling region and the handle of the medical device.

4. The device according to claim 1, wherein the coupling region is configured to snap-fit onto the handle of the medical device.

5. The device according to claim 1, wherein the coupling region is configured to wrap around the handle of the medical device.

6. The device according to claim 1, wherein the handle of the medical device is a first handle, and wherein the body includes a second handle, the actuator is movably coupled to the second handle.

7. The device according to claim 6, wherein the second handle includes an interior portion configured to receive a pressurized fluid container, the pressurized fluid container including the source of pressurized fluid.

8. The device according to claim 6, wherein a longitudinal axis of the second handle extends substantially parallel to a longitudinal axis of the first handle when the delivery device is coupled to the first handle.

9. The device according to claim 6, wherein the second handle is spaced from the first handle when the delivery device is coupled to the first handle.

10. The device according to claim 1, wherein the coupler is configured to form a fluid tight seal with the port of the channel such that the exit port is fluidically connected to the channel.

11. The device according to claim 1, wherein the coupler is a press-fit coupler configured to press fit onto the port to form a fluid tight seal with the port.

12. The device according to claim 1, wherein the coupler is a first coupler and the exit port is a first exit port, and further comprising:
a first catheter fluidically coupled to the first coupler at a first end;
a y-connector fluidically coupled to a second end of the first catheter;
a syringe fluidically coupled to the y-connector; and
a second coupler including a second exit port for aligning with a port of the channel; wherein the second exit port is fluidically connected to the first catheter, the y-connector, and the syringe; and wherein the second coupler is configured to mate with the port of the channel.

13. The device according to claim 12, further comprising a second catheter including a third coupler, wherein the second catheter is fluidically connected to the y-connector, coupled to the second coupler, and the third coupler is configured to mate with the port of the channel.

14. The device according to claim 1, wherein the handle of the medical device is a first handle, and wherein the body includes a first proximal portion including a second handle, a first distal portion, and a second proximal portion including the coupling region.

15. A delivery device configured to deliver an agent to a target tissue through a channel of a medical device, the delivery device comprising:
a body including (a) a coupling region configured to removably attach to a handle of the medical device, the medical device including an endoscope, and (b) a coupler including an exit port for aligning with a port of the channel, wherein the coupler is configured to mate with the port of the channel;
a pressurized fluid container within the body;
an enclosure within the body defined by a cylindrical portion and a funnel portion positioned at an end of the enclosure opposite to the cylindrical portion, and wherein the cylindrical portion is configured to store and feed the agent to the funnel portion via gravity, the funnel portion is configured to receive a pressurized fluid to move the agent within the cylindrical portion of the enclosure, and to direct and release a combination of the pressurized fluid and the agent through the exit port;
a regulator within the body and configured to control delivery of the pressurized fluid from the pressurized fluid container prior to the pressurized fluid entering the enclosure at the funnel portion, the regulator including a fluid input port coupled to the pressurized fluid container such that the pressurized fluid enters the regulator prior to entering the enclosure, wherein the pressurized fluid and the agent flows from the enclosure to the exit port upon the pressurized fluid from the pressurized fluid container entering the regulator via the fluid input port and prior to the cylindrical portion of the enclosure receiving the pressurized fluid from the regulator via the funnel portion; and
an actuator including a trigger, the actuator configured to pierce the pressurized fluid container by selectively moving a pin into engagement with the pressurized fluid container to release the pressurized fluid from the pressurized fluid container for receipt by the regulator via the fluid input port.

16. The delivery device according to claim 15, wherein a total volume of the pressurized fluid within the pressurized fluid container is configured to deploy a preset amount of the agent through the channel, and the agent includes a powder.

17. A system configured to deliver an agent to a target tissue through a channel of a medical device, the system comprising:
the medical device comprising an endoscope that includes a handle, the channel, and a port at an end of the channel; and
a delivery device comprising:
a body including (a) a coupling region configured to removably attach to the handle; and (b) a coupler including an exit port for aligning with the port, wherein the coupler is configured to mate with the port;
an input port disposed within the body;
a source of the agent disposed within the body, the source of the agent is defined by a funnel portion and a cylindrical portion positioned upstream from the funnel portion, the cylindrical portion is configured to feed the agent to the funnel portion via gravity, and the funnel portion is configured to direct the agent out of the cylindrical portion;
a source of pressurized fluid disposed within the body and in fluid communication with the agent stored in the cylindrical portion via the funnel portion, wherein the body, the source of agent, and the source of pressurized fluid are arranged to mix the agent and a pressurized fluid within the source of the agent, and deliver the mixture of the agent and the pressurized fluid to the exit port and the channel for delivery to the target tissue; and
an actuator including a trigger, the actuator configured to selectively release the pressurized fluid from the source of the pressurized fluid into the cylindrical portion through the funnel portion, in response to the input port piercing the source of pressurized fluid to release the pressurized fluid towards the source of the agent, upon actuation of pulling the actuator, the input port including a movable pin.

18. The system according to claim 17, wherein the delivery device is configured to deliver the agent and the pressurized fluid through the channel such that the agent contacts an interior surface of the channel.

19. The delivery device according to claim 15, wherein the enclosure includes a filter configured to prevent movement of the agent from the enclosure and towards the regulator via the fluid input port.

20. The system according to claim 17,
wherein the body, the source of the agent, and the source of the pressurized fluid are arranged to deliver the agent and the pressurized fluid from the cylindrical portion and downstream through the funnel portion prior to the agent and the pressurized fluid being received at the exit port and the channel.

* * * * *